(12) United States Patent
Burstein et al.

(10) Patent No.: US 6,620,198 B2
(45) Date of Patent: *Sep. 16, 2003

(54) COMPOSITE BEARING INSERTS FOR TOTAL KNEE JOINTS

(75) Inventors: Albert Burstein, Sarasota, FL (US); Raymond Cloutier, Warsaw, IN (US); C. Michael Mauldin, Lake City, FL (US)

(73) Assignee: Exactech, Inc., Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/413,783

(22) Filed: Oct. 7, 1999

(65) Prior Publication Data

US 2002/0055784 A1 May 9, 2002

(51) Int. Cl.⁷ .................................................. A61F 2/38
(52) U.S. Cl. .................................. 623/20.28; 623/20.15
(58) Field of Search ........................ 623/20.33, 20.34, 623/20.28, 20.15, 20.16, 20.32

(56) References Cited

U.S. PATENT DOCUMENTS

| | | | |
|---|---|---|---|
| 4,205,400 A | 6/1980 | Shen et al. | |
| 4,479,271 A | 10/1984 | Bolesky et al. | |
| 4,936,853 A | * 6/1990 | Fabian et al. | 623/20 |
| 5,019,103 A | * 5/1991 | Van Zile et al. | 623/20 |
| 5,080,675 A | 1/1992 | Lawes et al. | |
| 5,152,797 A | * 10/1992 | Luckman et al. | 623/20 |
| 5,194,066 A | * 3/1993 | Van Zile | 623/20 |
| 5,326,358 A | 7/1994 | Aubriot et al. | |
| 5,370,699 A | 12/1994 | Hood et al. | |
| 5,395,401 A | 3/1995 | Bahler | |
| 5,413,604 A | 5/1995 | Hodge | |
| 5,514,183 A | 5/1996 | Epstein et al. | |
| 5,776,200 A | 7/1998 | Johnson et al. | |
| 5,957,979 A | * 9/1999 | Beckman et al. | 623/20 |
| 6,139,581 A | * 10/2000 | Engh et al. | 623/20.34 |
| 6,214,052 B1 | * 4/2001 | Burkinshaw | 623/20.34 |
| 6,306,172 B1 | * 10/2001 | O'Neil et al. | 623/20.15 |

* cited by examiner

Primary Examiner—Bruce Snow
(74) Attorney, Agent, or Firm—Morgan & Finnegan LLP

(57) ABSTRACT

A composite bearing insert for a total knee joint or a unicondylar knee joint which minimizes or eliminates the production of wear debris resulting from relative motion at the interface between the endoskeleton and a tibial tray of a knee joint prosthesis. The composite bearing insert includes an endoskeleton and a polymer portion which is preferably molded into and locked within the endoskeleton. The endoskeleton is configured to be locked to a tibial component, such as a tibial tray or keel. The modularity of the assembly facilitates the interchangeability of various composite bearing inserts with various tibial components.

19 Claims, 6 Drawing Sheets

COMPOSITE BEARING INSERTS FOR TOTAL KNEE JOINTS

FIELD OF THE INVENTION

The present invention relates generally to medical devices and, more particularly, to a composite knee joint assembly for minimizing or eliminating the production of wear debris resulting from relative motion at the interface between the endoskeleton and tibial tray portions of a composite knee joint assembly.

BACKGROUND OF THE INVENTION

Knee surgery for the replacement and repair of a patient's knee has become relatively commonplace in recent years. Prosthetic knee joint devices are available from a variety of manufacturers. Such prosthetic systems, when properly installed, approximate a patient's natural knee movement.

Typical knee joint prostheses contain a femoral component and a tibial component. The femoral component typically has a generally concave surface portion for fixation and load transfer to the femur, with one or two convex condyles to allow articulation, restrict dislocation or sublixation, and transfer loads to the tibial component. Typical tibial components may be of unitary construction having a bearing surface to articulate with the femoral condyles, and a fixation surface to attach to the tibia by the use of grout, mechanical fixation or biological fixation. The tibial component may also be modular, containing a bearing insert portion and a backing platform portion, or tibial tray, for receiving the bearing insert portion and for affixation on a surgically prepared tibial plateau.

Currently available modular tibial components use a polymeric material for the bearing insert. Such currently available modular tibial components suffer from a tendency toward relative motion between the bearing insert portion and tibial tray. Such relative motion can cause wear in the generation of small particles from the polymeric bearing insert. Such wear can lead to failure of the knee joint prosthesis.

Various attempts to solve this problem include elaborate and often costly locking systems to minimize relative motion at the interface between the bearing insert and the metal tibial tray. In addition, such attempts at solving this problem have often not been modular and therefore have lost the advantages of modularity, including the possibility of interchangability of the bearing insert during surgery and the use of a screw to fix the tibial tray to surgically prepared tibial condyles.

Accordingly, there is a need for modular total knee joint prostheses and unicondylar knee joint prostheses which minimize or eliminate the production of wear debris resulting from relative motion at the interface between the polymer insert and metal tibial tray of knee joint prostheses.

SUMMARY OF THE INVENTION

The present invention fulfills the aforementioned need by providing a composite bearing insert for a total knee joint which minimizes or eliminates the production of wear debris that results from relative motion at the interface between the endoskeleton and the metal tibial tray of a total knee joint prosthesis.

In one embodiment of the present invention, a composite bearing assembly for a knee joint is provided, which includes a femoral component and a tibial component, wherein the tibial component includes a metal tibial element and a composite bearing insert structure attached to the metal tibial element. The composite bearing insert structure includes a polymeric bearing component interlocked with a metal endoskeletal component. The endoskeletal component is interlocked with the metal tibial element to minimize or eliminate the production of wear debris therebetween.

The composite bearing assembly may be configured such that the bearing insert contacts the tibial element, such as a tibial tray, only through metal-to-metal contact. In one embodiment of the invention, the polymer insert and tibial tray are interlocked through one or more interlocking dovetails. In various other embodiments of the invention, the tibial tray and bearing insert are interlocked through an interlocking screw arrangement.

The present invention also includes a technique for constructing composite bearing assemblies for total knee joints. In one embodiment of the present invention, the method includes (1) constructing an endoskeleton with a locking mechanism, (2) molding a polymeric powder to form and lock a polymeric bearing element to the metal endoskeleton, and (3) locking the endoskeleton to a tibial tray. In various embodiments of the invention, the locking mechanisms may include interlocking dovetails, a locking taper and/or an interlocking screw arrangement.

The details of the various embodiments of the present invention are set forth in the accompanying drawings and description below. Numerous additional features and advantages will become apparent from a review of the following details of various embodiments of the present invention.

DETAILED DESCRIPTION OF VARIOUS EMBODIMENTS OF THE PRESENT INVENTION

Figure 1:
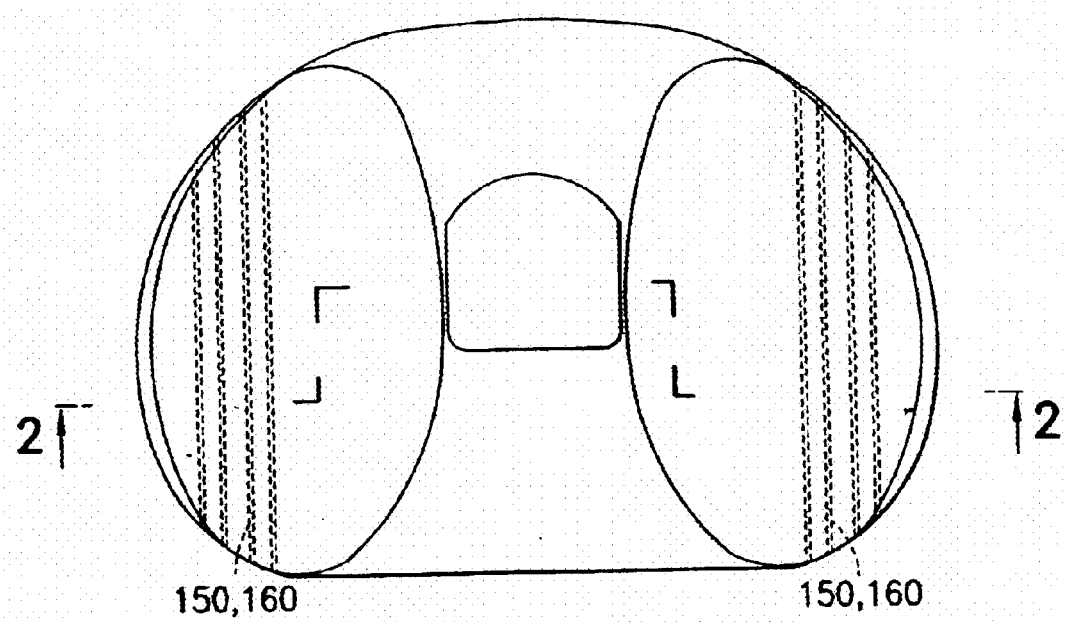
FIG. 1 is a top view of a composite bearing assembly for a total knee joint in accordance with one embodiment of the present invention.

With reference to the drawings, various embodiments of the present invention will now be shown and described. The leading numeral of each reference numeral indicates the first drawing in which that reference numeral is introduced. The trailing numerals of each reference number are consistently used throughout the drawings to designate counterpart or like elements.

With reference to FIG. 1, a cross-sectional view of a composite bearing assembly in accordance with one embodiment of the present invention is shown. In general, the composite bearing assembly 100 of the present invention consists of two elements: a tibial tray 110 and a composite bearing insert 120, each of which will now be described in greater detail below.

The tibial tray 110 is preferably made of a suitable, bio-compatible material that is suitable for fixation to surgically prepared tibial condyles through biologic, mechanical or grouting fixation. The tibial tray 110 may be made of metal, such as titanium or titanium alloy, cobalt-chrome alloy, or a suitable low corrosion iron alloy. In the alternative, the tibial tray 110 may be made of biocompatible polymer, ceramic, or a composite material of suitable strength and stiffness.

The second component of the composite bearing assembly 100 is a composite bearing insert 120 made of an endoskeleton 130 and a polymer bearing element 140. The polymer bearing element 140 is the bearing portion of the composite bearing insert 120, and is made of a suitable polymeric bearing material such as ultra high molecular weight polyethylene. The endoskeleton 130 is made of a stronger, stiffer material such as a biocompatible metal, composite or ceramic (which can be the same materials used for tibial tray 110). As such, the composite bearing insert 120 is a composite structure of a polymer and a stiffer, stronger material.

The polymer bearing element 140 forms a bearing surface 145 which receives the condyles of a femoral component (not shown) of a knee joint prosthesis. The polymer bearing element 140 is interlocked with the endoskeleton 130 through dovetails 150, thereby eliminating meaningful relative motion between the endoskeleton 130 and the polymer bearing element 140. In the alternative, mechanical, chemical or adhesive bonding may be used to interlock the endoskeleton 130 and the polymer bearing element 140. The elimination of such meaningful relative motion minimizes or eliminates the production of wear debris that results from relative motion at the interface between the endoskeleton 130 and the polymer bearing element 140.

Figure 2:
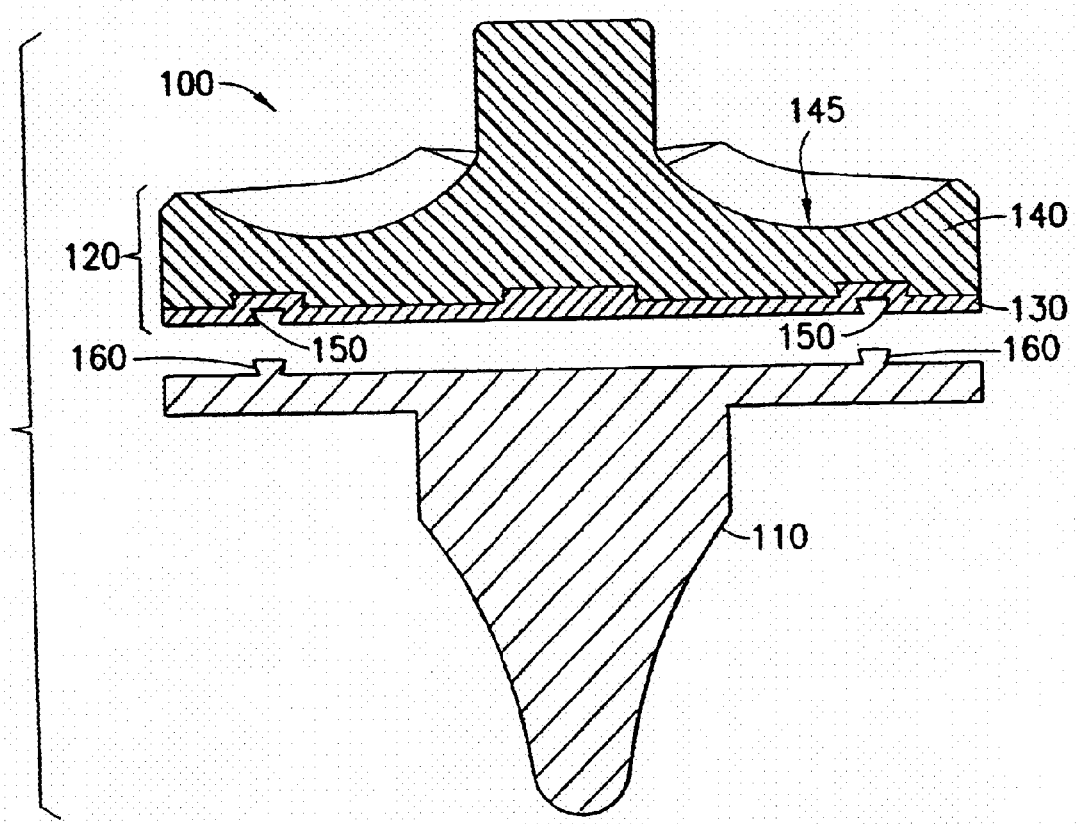
FIG. 2 is a cross-sectional view of the composite bearing assembly of the embodiment of FIG. 1 along lines 2—2.

With continuing reference to FIG. 1 and with reference to FIG. 2, the tibial tray 110 also has dovetails 160 which interlock with dovetails 150 of the composite bearing insert 120 to eliminate meaningful relative motion between the tibial tray 110 and the composite bearing insert 120. As shown in the embodiment of FIG. 1, the composite bearing insert 120 may be configured so that it contacts the tibial tray 10 only by metal-to-metal contact. As such, the present invention minimizes the generation of wear debris by eliminating contact between any polymer surface on the composite bearing insert 120 and any metal surface on the tibial tray 110.

As will be described in greater detail below, the tibial tray 110 may be interlocked with the composite bearing insert 120 through a number of alternate techniques including screws or pin fasteners, locking bayonets, or snap rings, and may also include various tapered arrangements. It is also to be understood that the configuration and number of dovetails 150, 160 may be altered within the scope of the present invention. For example, although the composite bearing insert 120 has two interlocking dovetails, it is to be understood that one, three, or more dovetails may be used. In addition, although dovetails 150 are shown as female dovetails, and dovetails 160 are shown as male dovetails, it is to be understood that the interlocking arrangement of FIG. 1 may be inverted so that dovetails 150 are male elements, and dovetails 160 are female elements.

Figure 3:
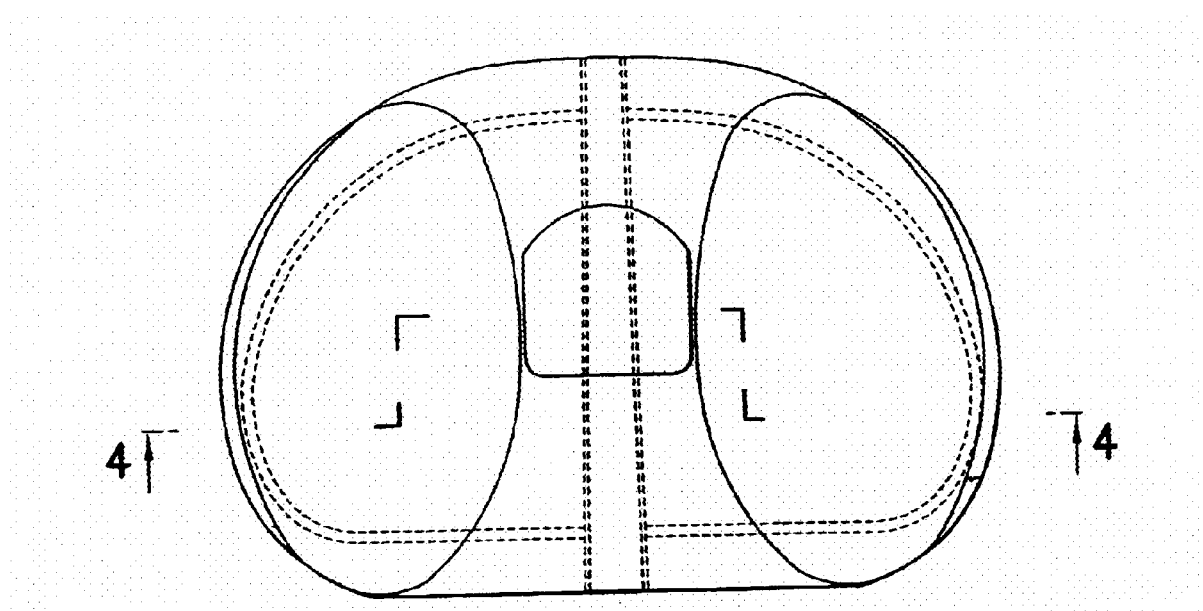
FIG. 3 is a top view of an alternate embodiment of a composite bearing assembly in accordance with another embodiment of the present invention.
Figure 4:
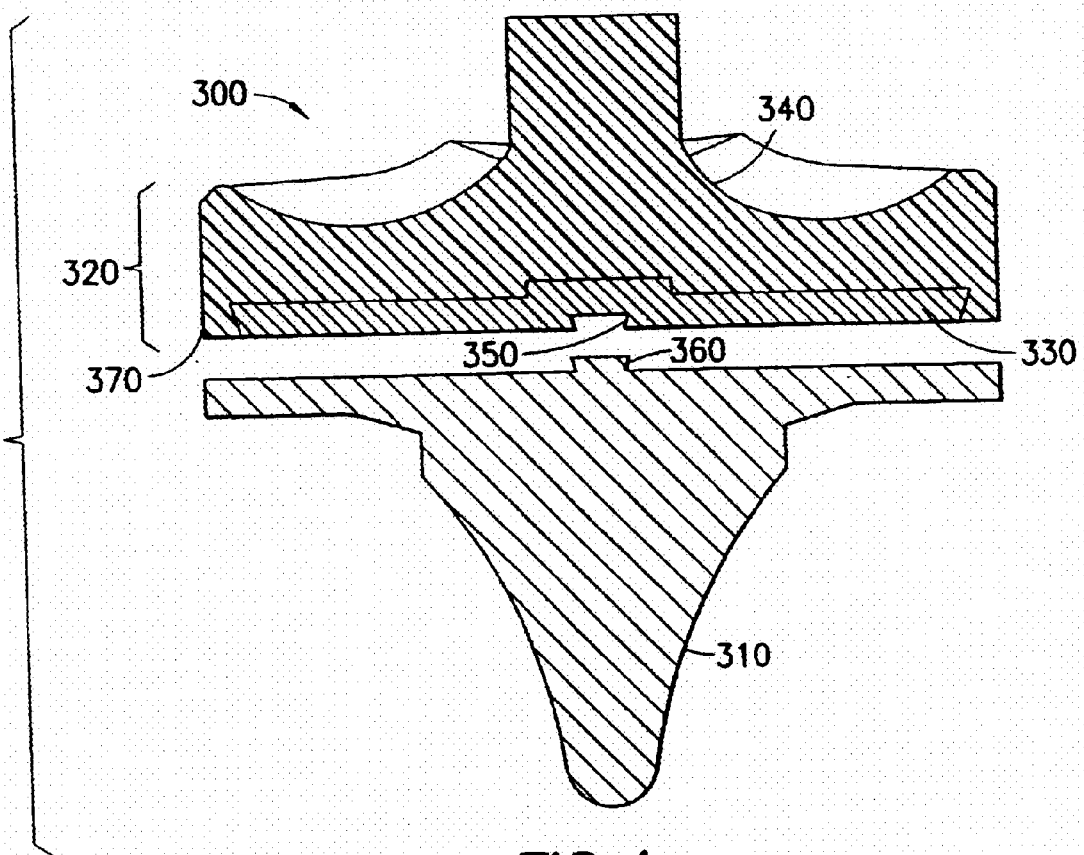
FIG. 4 is a cross-sectional view of the composite bearing assembly of the embodiment of FIG. 3 along lines 4—4.

With reference to FIGS. 3 and 4, an alternate embodiment of the composite bearing assembly 300 is shown. As with the previous embodiment, composite bearing assembly 300 includes a tibial tray 310, a composite bearing insert 320, an endoskeleton 330, a bearing element 340, and dovetails 350, 360. The composite bearing assembly 300 also includes a tapered rim lock 370 to securely lock the polymer bearing element 340 to the endoskeleton 330.

Figure 5:
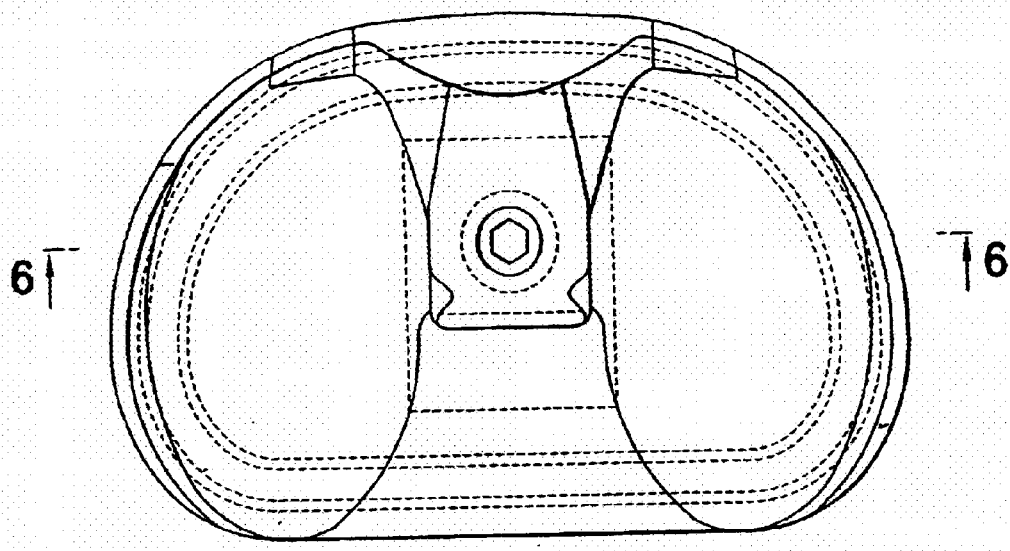
FIG. 5 is a top view of an alternate embodiment of a composite bearing assembly in accordance with another embodiment of the present invention.
Figure 6:
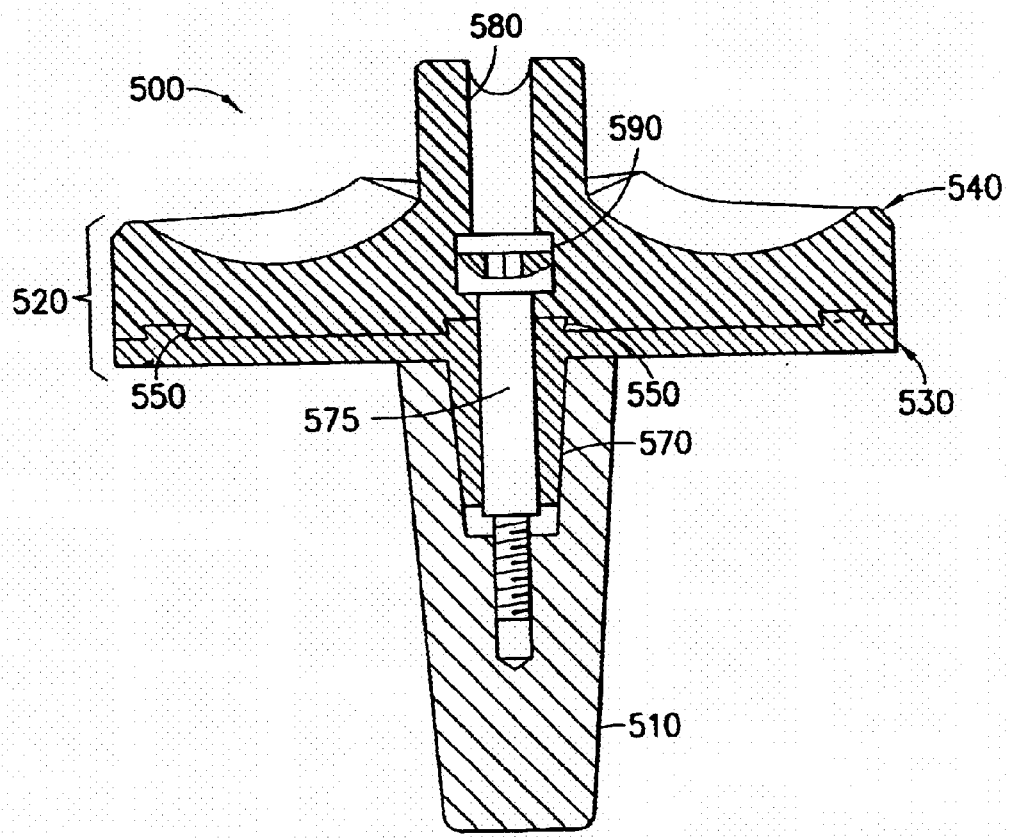
FIG. 6 is a cross-sectional view of the composite bearing assembly of the embodiment of FIG. 5 along lines 6—6.

With reference to FIGS. 5 and 6, an alternate embodiment of the present invention is shown. Composite bearing assembly 500 includes a tibial keel 510, and a composite bearing insert 520. Tibial keel 510 may be trapezoidal, finned or may be a stem extension. It is to be understood however that the modular keel 510 may have any of a number of different shapes. Composite bearing insert 520 includes an endoskeleton 530 and a bearing element 540. Composite bearing insert 520 also includes dovetails 550 interlocking endoskeleton 530 and bearing element 540. Composite bearing insert 520 also includes a molded/encapsulated locking screw 575, a clearance hole 580 which is configured to receive a wrench (not shown), and a second clearance hole 590. The locking screw 575 secures the composite bearing insert 520 to the tibial keel 510. The endoskeleton 530 may also include a locking taper 570 to assist in interlocking the endoskeleton 530 with the modular keel 510. The locking screw 575 may also be extended proximally to act as a support post for a constrained condylar knee.

Figure 7:
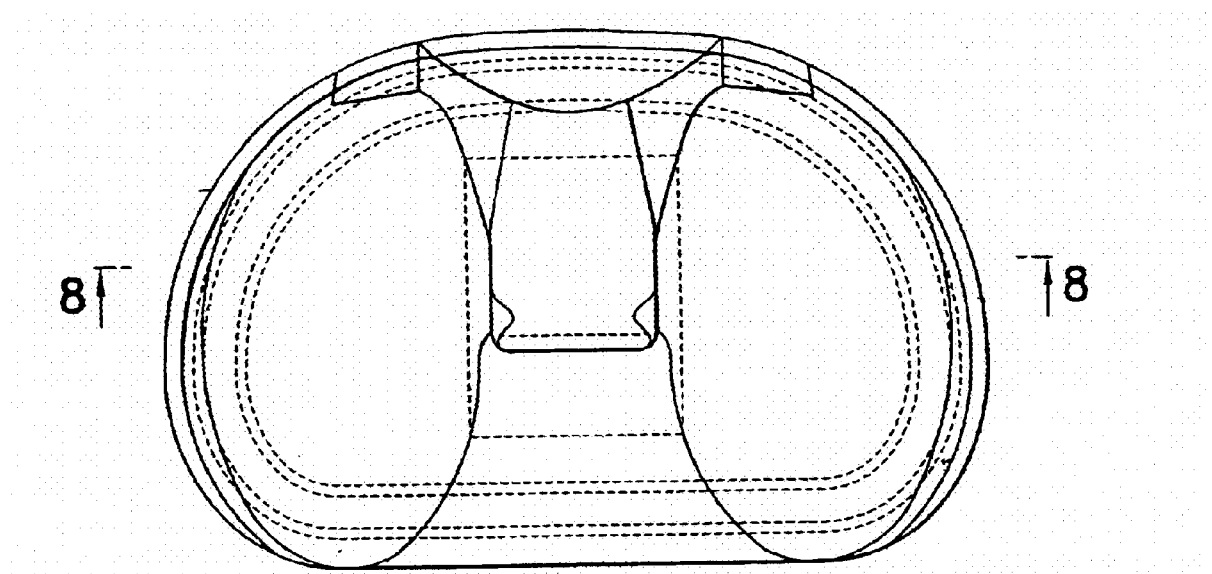
FIG. 7 is a top view of an alternate embodiment of a composite bearing assembly in accordance with another embodiment of the present invention.
Figure 8:
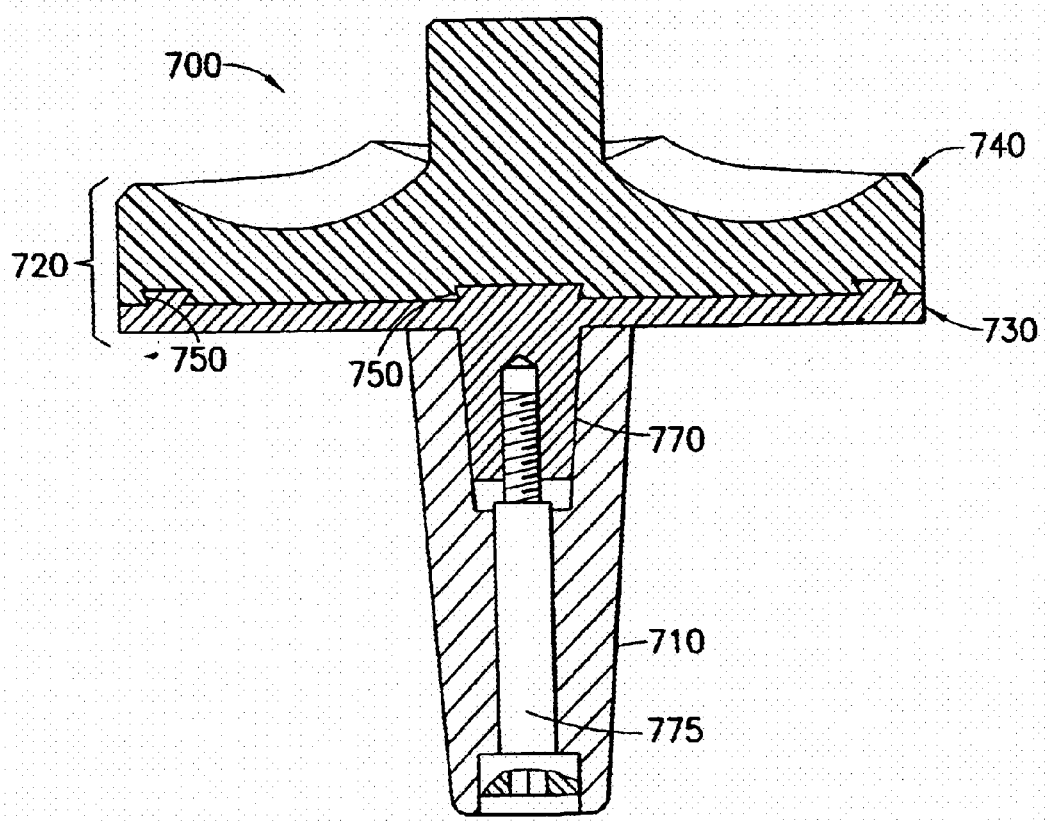
FIG. 8 is a cross-sectional view of the composite bearing assembly of the embodiment of FIG. 7 along lines 8—8.

With reference to FIGS. 7 and 8, another embodiment of the present invention is shown. Composite bearing assembly 700 includes a tibial keel 710, and a composite bearing insert 720. Tibial keel 710 may be trapezoidal, finned or may be a stem extension. It is to be understood however that the modular keel 710 may have any of a number of different shapes. Composite bearing insert 720 includes an endoskeleton 730 and a bearing element 740. Composite bearing insert 720 also includes dovetails 750 interlocking endoskeleton 730 and bearing element 740. The modular keel 710 also includes an encapsulated locking screw 775 which secures the composite bearing insert 720 to the tibial keel 710. The endoskeleton 730 may also include a locking taper 770 to assist in interlocking the endoskeleton 730 with the modular keel 710.

Figure 9:
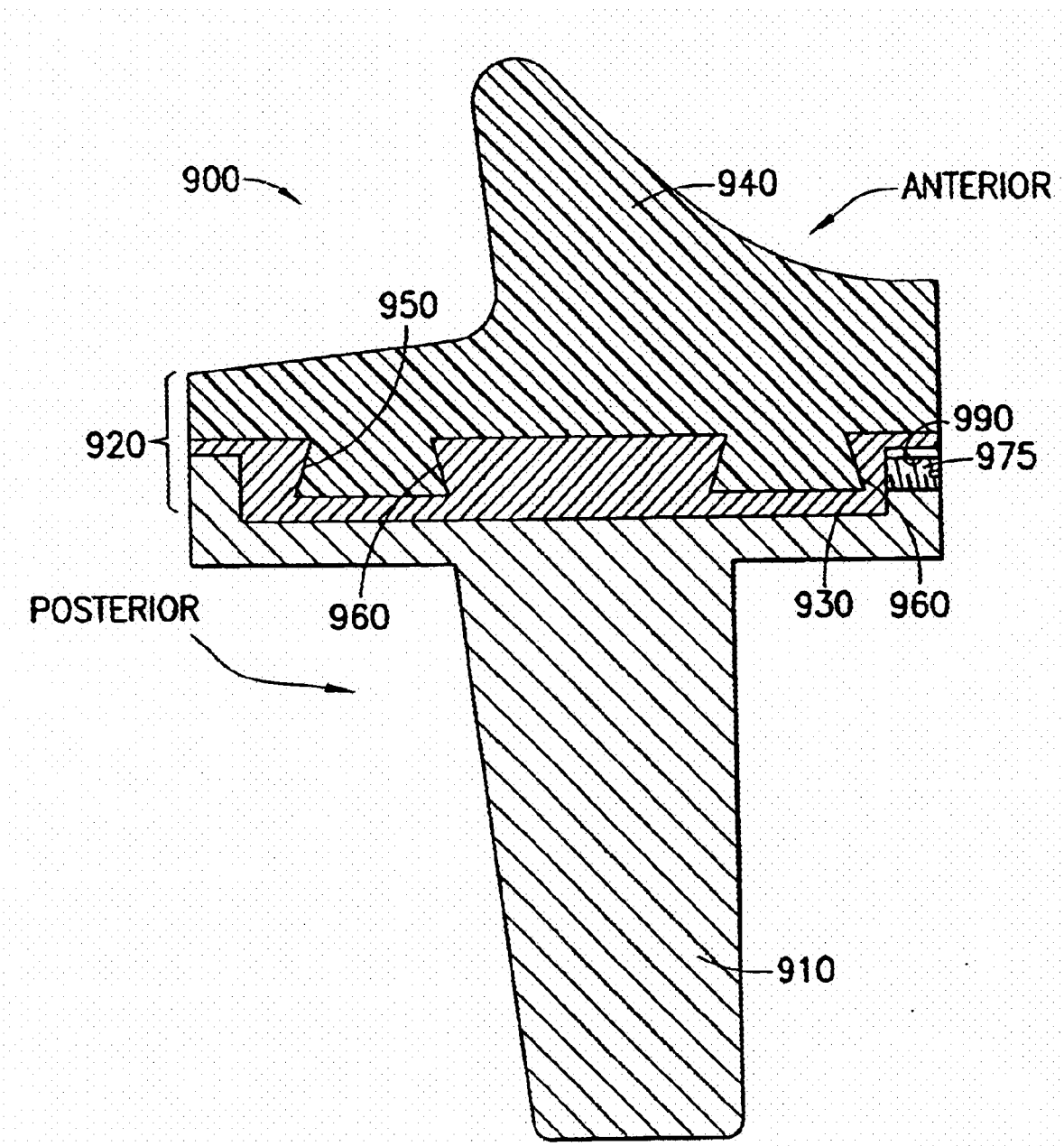
FIG. 9 is a cross-sectional view of an alternate embodiment of a composite bearing assembly in accordance with another embodiment of the present invention.

With reference to FIG. 9, an alternate embodiment of the composite bearing assembly 900 is shown. As with the previous embodiment, composite bearing assembly 900 includes a tibial tray 910, a composite bearing insert 920, an endoskeleton 930, a bearing element 940, and dovetails 950, 960. The composite bearing assembly 900 also includes a set screw 975 disposed within a threaded hole 990 to push the endoskeleton 930 against dovetail 960 to lock the composite bearing insert 920 to the tibial tray 910.

Figure 10:
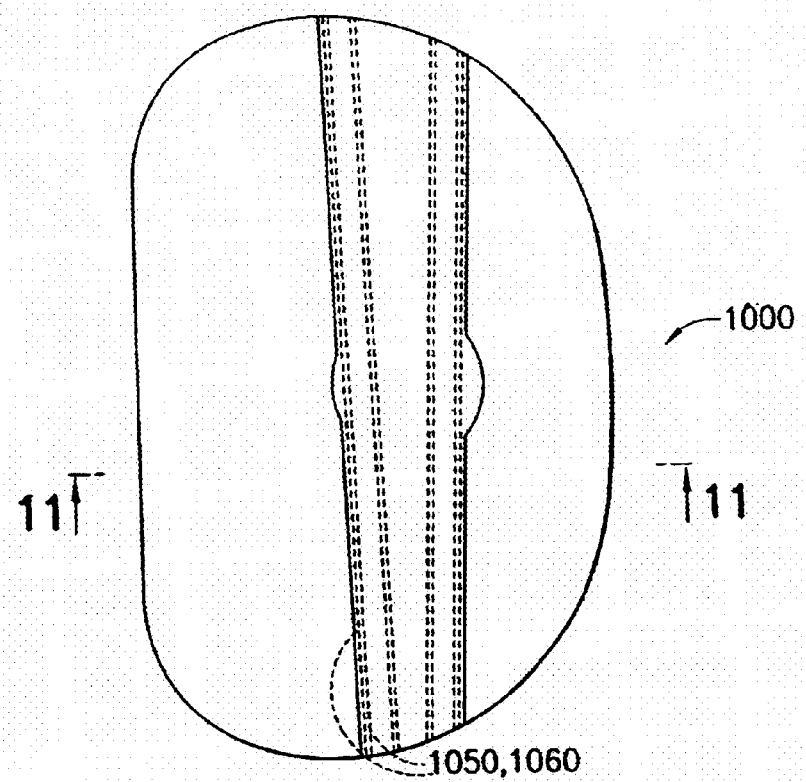
FIG. 10 is a top view of an alternate embodiment of a composite bearing assembly in accordance with another embodiment of the present invention.
Figure 11:
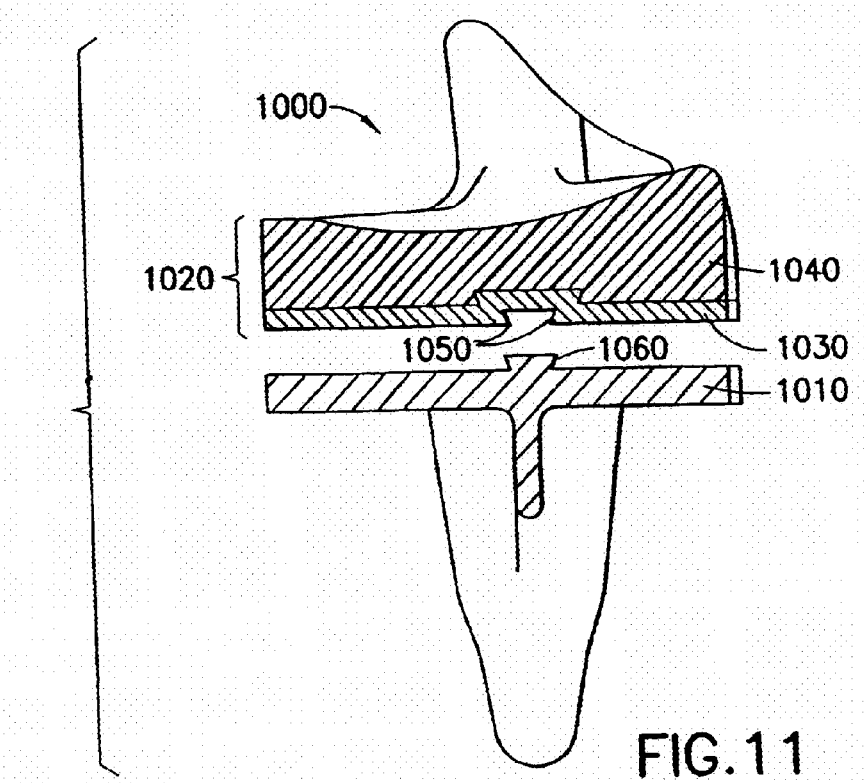
FIG. 11 is a cross-sectional view of the composite bearing assembly of the embodiment of FIG. 10 along lines 11—11.

With reference to FIGS. 10 and 11, another embodiment of the composite bearing assembly 1000 of the present invention is shown. As with previous embodiments, composite bearing assembly 1000 includes a tibial tray 1010, a composite bearing insert 1020, an endoskeleton 1030, a bearing element 1040, and dovetails 1050, 1060. The upper dovetail 1050 locks the endoskeleton 1030 to the bearing element 1040. The lower dovetail 1060 locks the endoskeleton 1030 to the tibial tray 1010.

Method of Manufacture

In manufacturing the composite bearing liner element of the present invention, one method includes attaching a polymer bearing element (such as element 140) to a metal endoskeleton (such as element 130) by molding, such as by compression molding. Preferably, the polymeric material used is ultra-high molecular weight polyethylene.

In implementing this method, the metal endoskeleton may be suitably shaped or surfaced to securely interlock with, or bond to, the polymer bearing element. As previously discussed, one locking technique involves providing wedge-shaped mating surfaces at the endoskeleton/polymer junction so as to mechanically lock the two portions by the action of the shrinking of the polymer about the endoskeleton at the time of molding. This locking technique could involve the formation of dovetails, such as the dovetails 150 shown in FIG. 1. These techniques effectively interlock the endoskeleton and polymer liner, thereby preventing relative movement therebetween. Once the endoskeleton and polymer bearing element have been interlocked to form a composite bearing insert, the composite bearing insert may then be interlocked with a tibial component, such as a tibial keel or tray.

By the aforementioned detailed description and the attached drawings, a number of embodiments of the present invention have been shown and described. It is to be understood that various modifications may be made without departing from the spirit and scope of the invention. Accordingly, it is to be understood that the invention is not to be limited by the illustrated and described embodiments, but by the scope of the appended claims.

What is claimed is:

1. A modular composite bearing assembly for a knee joint, comprising:

a metal tibial element and a composite bearing insert structure attached to the metal tibial element, said composite bearing insert structure including a polymeric bearing component interlocked with a metal endoskeletal component, wherein said endoskeletal component is interlocked with said metal tibial element to prevent relative movement therebetween, and wherein said polymeric bearing component is configured to operatively engage a femoral component.

2. The composite bearing insert of claim 1 wherein at least a portion of said endoskeletal component is shaped to securely interlock with said polymeric bearing insert.

3. The composite bearing insert of claim 1 wherein said polymeric bearing component is made from polyethylene.

4. The composite bearing insert of claim 1 wherein said endoskeletal component is made of a material selected from the group consisting of titanium, titanium alloy, cobalt-chrome alloy ceramic, biocompatible composite, polymer, and steel alloy.

5. The composite bearing insert of claim 1 wherein said femoral component includes a plurality of condyles, and wherein said polymeric bearing component is configured to operatively engage said condyles.

6. The composite bearing insert of claim 1 wherein said metal tibial element is adapted for fixation to a surgically prepared tibia using a technique selected from the group consisting of biologic fixation, mechanical fixation, and grouting fixation.

7. The composite bearing insert of claim 1 wherein said polymeric bearing insert is interlocked with said metal endoskeletal component through an interlocking structure selected from the group consisting of a mechanical interlock, a chemical interlock, and an adhesive bond.

8. The composite bearing insert of claim 1 wherein said polymeric bearing component is a compression molded polymeric bearing component.

9. The composite bearing insert of claim 1 wherein said endoskeletal component and said tibial element are interlocked through a mechanism selected from the group consisting of a taper lock, a screw and a pin.

10. The composite bearing insert of claim 1 wherein said tibial element is a tibial tray.

11. The composite bearing element of claim 1 wherein said tibial element includes a tibial keel.

12. The composite bearing insert of claim 1 wherein said composite bearing component is a composite bearing insert.

13. A method of constructing a modular composite bearing assembly for a knee joint, comprising:

constructing a metal tibial component;

constructing a metal endoskeleton component;

molding a polymeric bearing component to interlock the polymeric bearing component to the metal endoskeleton component to form a composite bearing component; and interlocking the composite bearing component to said tibial component to prevent relative movement therebetween.

14. The method of claim 13 wherein said tibial component is a tibial tray.

15. The composite bearing element of claim 13 wherein said tibial element includes a tibial keel.

16. The method of claim 13 wherein said composite bearing component is interlocked with said tibial component such that said composite bearing component contacts said tibial component only though metal to metal contact.

17. The method of claim 13 wherein wherein said composite bearing component is interlocked with said tibial component through at least one of: screw fixation and an interlocking dovetail.

18. The method of claim 13 wherein said polymeric bearing component is interlocked with a metal tibial component through at least one of: screw fixation and an interlocking dovetail.

19. A modular composite bearing assembly for a knee joint, comprising:

metal tibial element means and composite bearing insert structure means attached to the metal tibial element means, said composite bearing insert structure means including polymeric bearing component means interlocked with metal endoskeletal component means, wherein said endoskeletal component means is interlocked with said metal tibial element means to prevent relative movement therebetween, wherein said polymeric bearing component means is configured to operatively engage a femoral component, and wherein said modular composite bearing assembly is configured for attachment to the tibia of a patient.

* * * * *